United States Patent
Flohr et al.

(10) Patent No.: US 6,327,326 B1
(45) Date of Patent: Dec. 4, 2001

(54) METHOD FOR IMAGE RECONSTRUCTION FOR A COMPUTED TOMOGRAPHY APPARATUS

(75) Inventors: Thomas Flohr, Uehlfeld; Bernd Ohnesorge; Heinrich Wallschlaeger, both of Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/448,551

(22) Filed: Nov. 23, 1999

(30) Foreign Application Priority Data

Nov. 25, 1998 (DE) .............................. 198 54 438

(51) Int. Cl.[7] ........................................ A61B 6/03
(52) U.S. Cl. ................... 378/8; 378/15; 378/94
(58) Field of Search ................................ 378/4, 8, 15, 94

(56) References Cited

U.S. PATENT DOCUMENTS 4,707,822 * 11/1987 Hopkinson et al. .................. 378/14
6,233,478 * 5/2001 Liu ...................................... 600/428

FOREIGN PATENT DOCUMENTS 0 426 464  5/1991 (EP).

* cited by examiner

*Primary Examiner*—David V. Bruce
(74) *Attorney, Agent, or Firm*—Schiff Hardin & Waite

(57) ABSTRACT

In a method for image reconstruction in a computed tomography apparatus, whereby only the minimally possible projection angle range $\alpha_g(\beta)$ for the respective fan angle $\beta$ is employed for all measured values $S(\beta, \alpha)$ of the same fan angle $\beta$.

14 Claims, 6 Drawing Sheets

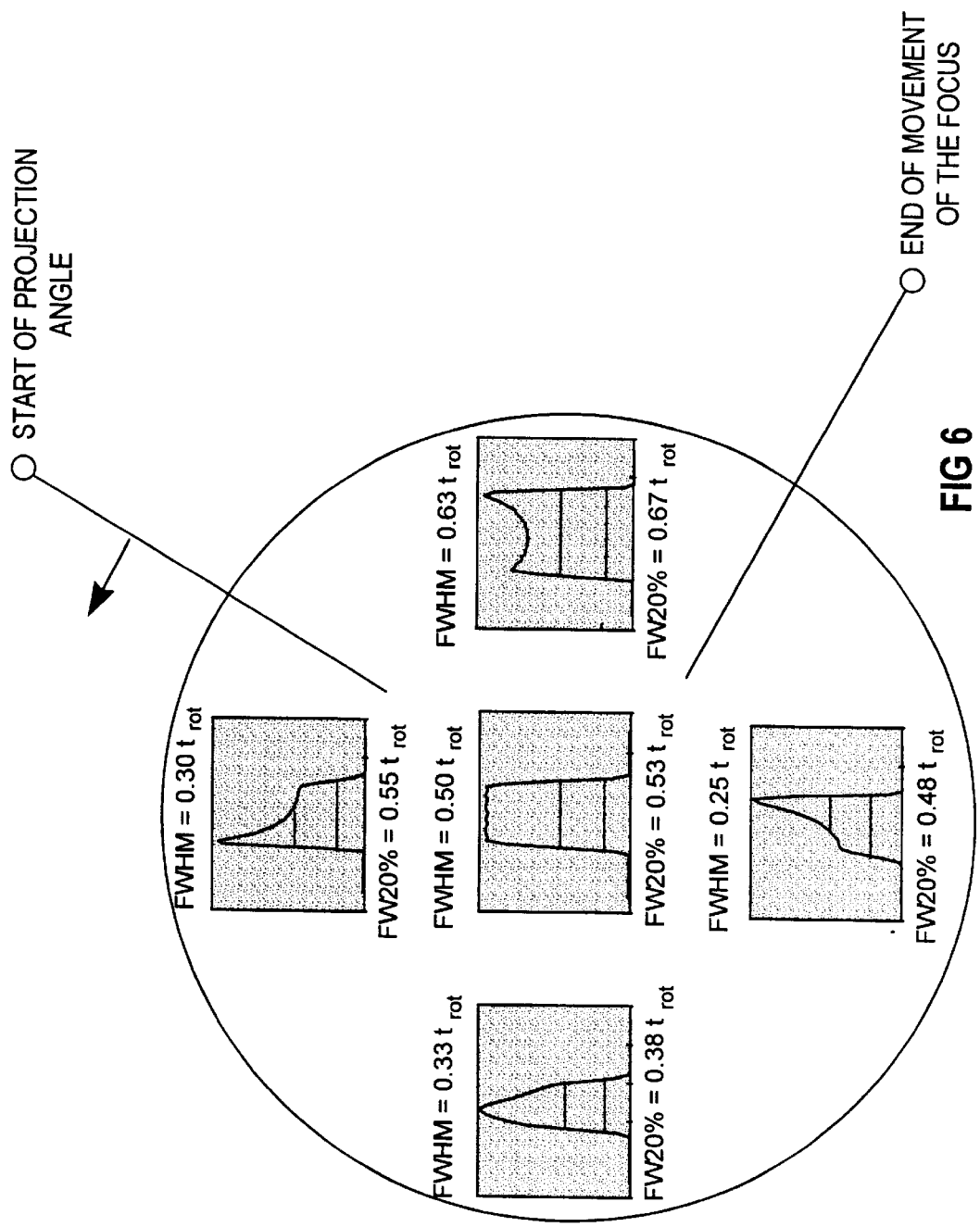

METHOD FOR IMAGE RECONSTRUCTION FOR A COMPUTED TOMOGRAPHY APPARATUS

BACKGROUND OF THE INVENTION

1. Field of the Invention

The present invention is directed to a method for image reconstruction in a computed tomography apparatus of the type wherein measured values S(β, α) are obtained by a radiation source in fan geometry that is movable around a system axis around a measuring field in which an examination subject is disposed, wherein α is the projection angle and β is the fan angle of the measured values, and wherein only the minimally possible projection angle range $\alpha_g(\beta)$ for the respective fan angle β is employed for all measured values S(β, α) of the same fan angle β, with the minimally possible projection angle range $\alpha_g(\beta)$ being established by the equation $\alpha_g(\beta)=\Pi-2\beta$.

2. Description of the Prior Art

When imaging time-variable processes, a high time resolution of the presentation is of great significance. In the field of computed tomography, time-variable events are, for example, movements of the heart muscle or of the heart valves, movements in the mediastinum induced by the heart activity or peristaltic movements. Known methods for improving time resolution in computed tomography exposures are sub-revolution exposures with a computed tomography system of the third or fourth generations, or exposures with an electron beam tomography (EBT) apparatus.

The measuring time interval $t_Q$ from which measured values take effect in an image serves as rough measure for the time resolution realized in an image. More precise statements with respect to the time resolution are possible on the basis of time sensitivity profiles.

A reduction of the measuring time interval $t_Q$ can ensue either by reducing the angular range to be swept when scanning an examination subject given a constant angular velocity, or by increasing the angular velocity of the scan given a constant angular range. The first possibility is used in sub-revolution exposures, namely for also shortening the measuring time interval $t_Q$ by registering measured values over less then 360°.

When the measured values S(β, α) according to FIG. 1 (which can also be employed to practice the invention) are registered in fan geometry (β is the fan angle; α is the projection angle), then the condition for a minimal projection angle range is formulated as follows. Given a full revolution (simple revolution) of 2Π, there is a complementary measured value $S(\bar{\beta};\bar{\alpha})$, for each measured value S(β,α) characterized by α and β, this having been registered from the opposite direction. This complementary measured value is redundant. It is therefore obviously allowable to select that projection angle range as minimal projection angle range for each β that happens to contain no complementary measured values at the moment. The attenuation value $S(\bar{\beta};\bar{\alpha})$complementary to S(β,α) is the attenuation value given the angles $$\bar{\alpha}=\alpha+2\beta\pm\Pi, \bar{\beta}=-\beta. \quad (1)$$

Enough measured values must then be available for each fan angle β so that the remainder up to 2Π contains only complementary values. For the minimal revolution angle $\alpha_g(\beta)$, i.e. the minimal projection angle range, $$\alpha_g(\beta)=\Pi-2\beta \quad (2)$$

applies.

The equality $\alpha_g(\beta=0)=\Pi$ arises for the central channel of the detector (α=0). However, $\alpha_g(-\beta_{fan}/2)=\Pi+\beta_{fan}$ is required for the channel $\beta=-\beta_{fan}/2$ ($\beta_{fan}$ is the overall fan angle of the detector), i.e. a larger projection angle range than Π. The channel $\beta=\beta_{fan}/2$ of the projection angle range $\alpha_g(-\beta_{fan}/2)=\Pi-\beta_{fan}$ is adequate for this purpose.

The maximally required projection angle range $\alpha_g(-\beta_{fan}/2)=\Pi+\beta_{fan}$ has been employed for all fan angles β in conventional sub-revolution reconstructions. This projection angle range, however, is only really required for the channel $\beta=-\beta_{fan}/2$; by contrast thereto, there are direct as well as complementary measured values in a part of the projection angle range for all other fan angles that are suitably averaged for reasons of dose utilization.

In order to reduce line artifacts, a discontinuous transition between direct and complementary measured values is often avoided by a soft transition weighting having the width $\alpha_{trans}$. The necessary projection angle range is enlarged by $\alpha_{trans}$ as a result. Conventionally, thus, the projection angle range $$\alpha_Q=\Pi+\beta_{fan}+\alpha_{trans} \quad (3)$$

is employed for all fan angles β for sub-revolution reconstruction and not only for $\beta=-\beta_{fan}/2$. This is obvious since this projection angle range is in fact registered in the measurement for all fan angles. The conventional sub-revolution reconstruction therefore is optimized with respect to the dose utilization of a sub-revolution exposure, but is not optimized with respect to the best possible time resolution, as is required given exposures of moving subjects (for example, a beating heart).

In conventional sub-revolution reconstruction, the measuring time interval $$t_Q = \frac{\alpha_Q}{2\pi}t_{rot} \quad (4)$$

contributes to the image for each picture element. The time $t_{rot}$ is the time for a full revolution of the scanner. For example, $t_Q$ amounts to $t_Q=0.5s=0.66\ t_{rot}$ for all picture elements with $t_{rot}=0.75s$, $\beta_{fan}=52°$ and $\alpha_{trans}=8°$.

Conventional sub-revolution exposures in fan geometry thus have two disadvantages with respect to the time resolution. First, an exposure time of only half a second is achieved even given the fastest computed tomography systems of the third or fourth generations currently available, which still is not sufficient given higher pulse rates in order, for example, to be able to calculate a cardiac exposure during the relaxation phase. Second, the sequential registration of successive sub-revolution exposures prevents a rapid time scanning of the event of interest.

When the measured values S(p, ⊖) (p is the spacing of the line integral from the rotational center of the computed tomography system (⊖ is the projection angle) are already registered in parallel geometry, then it is sufficient to cover only a projection angle range of Π. Accordingly, an image-effective exposure time (measuring time interval) of $t_Q=0.5\ t_{rot}$ can be achieved. No apparatus is currently known, however, that can register true parallel data in one second or less. This possibility is thus eliminated for practical use.

The concept underlying electron beam tomography is to increase the angular velocity of the scan by suppressing mechanical components in order to reduce the measuring time interval $t_Q$. Systems have been produced that require only 50 ms for an individual scan of the patient. These systems, however, have two disadvantages. First, their costs are considerably higher than those of conventional computed tomography systems. Second, a number of scans of the subject are usually required for calculating images that do not have an excessively high noise level, as a result of which the gain in the reduction of the exposure time is reduced.

A method of the type initially described is disclosed in European Application 0 426 464. This method offers the advantage of a short calculating time since no more measured values than are absolutely required are employed.

SUMMARY OF THE INVENTION

An object of the present invention is to provide a method of the type initially described that enables a presentation of structures of an examination subject with improved time resolution.

The inventive method is based on the recognition that, because no more measured values than are absolutely required are employed, by virtue of using the smallest possible projection angle range for each fan angle β in the calculation of an individual image, regions of different time resolution are present in the measurement field. The inventive method utilizes this fact to image specific regions of an examination subject with a desired time resolution.

In the inventive method the examination subject is positioned in the measuring field before the registration of the measured values so that the diagnostically relevant region of the examination subject lies in a region of the measuring field wherein a desired time resolution is present; and/or measured values are registered for each projection angle such that a desired time resolution is achieved in that region of the measuring field wherein a diagnostically relevant region of the examination subject is located; and/or more measured values are registered than are required solely for image reconstruction of a diagnostically relevant region of the examination subject, and the image reconstruction ensues using measured values that are selected so that a desired time resolution is present in that region of the measuring field wherein the diagnostically relevant region is located.

The facts are respectively utilized in the version of inventive method that the measuring time interval contributing to the reconstruction of a picture element is dependent, among other things, on the position of the region to be imaged in the measuring field, and that the time resolution present at the individual points in the measuring field is also dependent on the reconstruction start angle, i.e. on that projection angle from which measured values are utilized for image reconstruction or, and that a time-optimized selection of the measured values is possible when more measured values are available than are required solely for imaging.

The registration of the measured values ensues in fan geometry because this is the fastest type of registration after electron beam tomography. The registration of the measured values can ensue in sub-revolutions, single revolutions or multiple revolutions; in the latter case, it can also ensue with a displacement of the radiation source and the examination subject relative to one another in the direction of the system axis (spiral scan). In particular, the registration of the measured values in multiple revolutions also makes it possible to calculate many images in an arbitrarily adjustable time interval for fast time scanning.

For reducing motion or spiral artifacts, it can be expedient to employ a transition region of freely selectable width in addition to the minimally possible projection angle range, with a suitable, smooth attenuation function that drops from 1 to 0 being applied in this transition region.

Although the measurement of the measured values ensues in fan geometry in the inventive method, the actual image reconstruction can ensue both in fan geometry as well as in parallel geometry according to known re-binning techniques.

In a further version of the invention, images are reconstructed that exhibit such time intervals from one another so that they are suitable for cinematic presentation.

In a preferred embodiment of the invention, the acquisition of the ECG signal of the examination subject ensues parallel to the registration of the measured values, which allows the time position of the measurement interval to be selected relative to the ECG signal of the examination subject, taking the QRS complex of the ECG signal into consideration. In this way, it is possible to select (or adjust) the time position of the measuring interval relative to the QRS complex such that a presentation of the heart of the examination subject that is low in motion artifacts is possible. This also applies to that case wherein the beginning of the measuring time interval is triggered by the ECG signal given acquisition of the ECG signal, of the examination subject in parallel with the registration of the measured values.

The inventive method thus enables a presentation of moving objects, for example of the beating heart with fewer image artifacts. In this presentation, the measuring time interval contributing to the reconstruction in parts of the measuring field is smaller than half the rotation time of the scanner and, as already mentioned, the measuring time interval contributing to the reconstruction of a picture element is dependent on the position of the picture element in the measuring field and on the reconstruction start angle.

DESCRIPTION OF THE DRAWINGS

FIG. 6 shows the dependency of the time-sensitive profile on the relationship between picture element and reconstruction start angle given parallel reconstruction.

DESCRIPTION OF THE PREFERRED EMBODIMENTS

Figure 1:
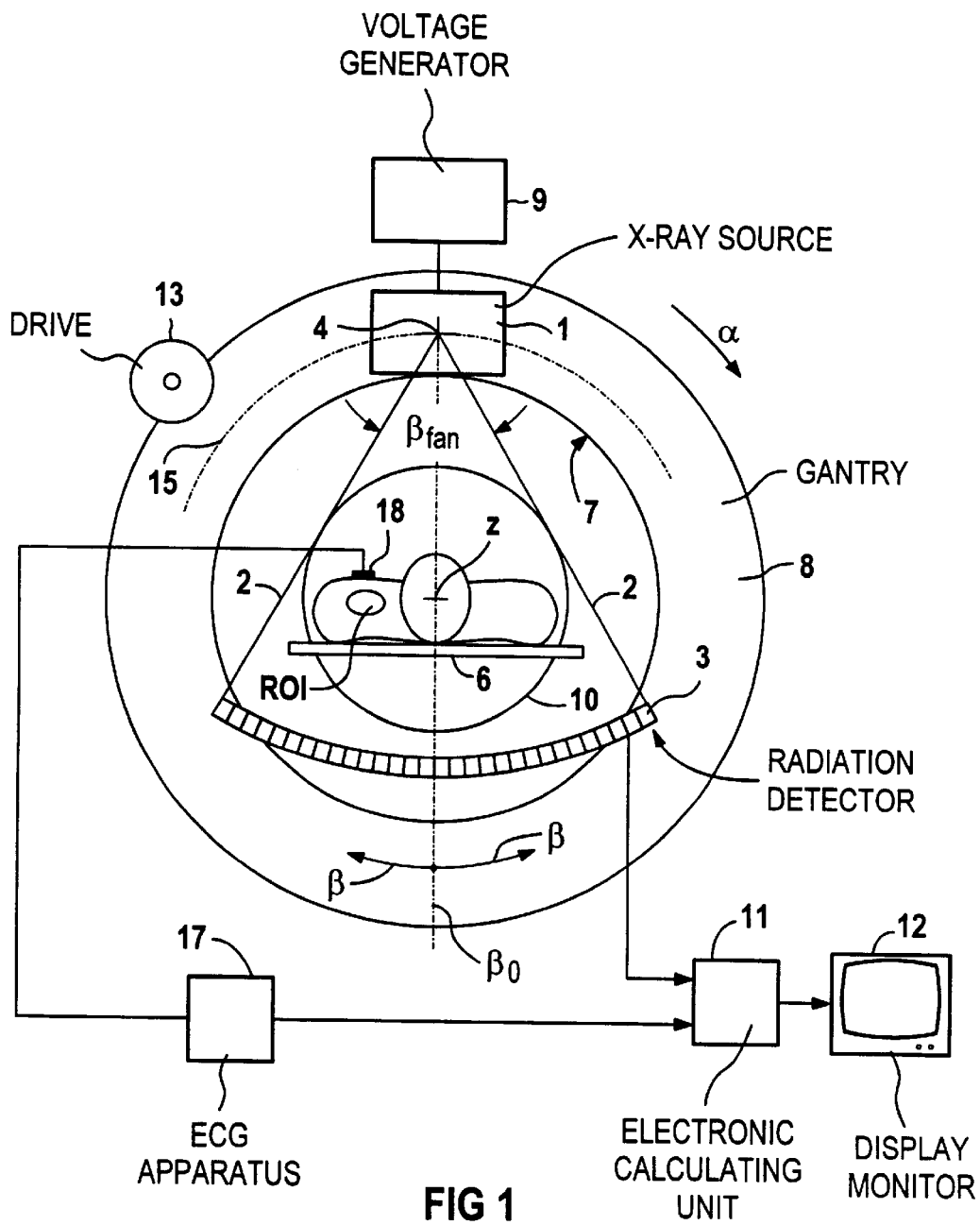
FIG. 1 is a schematic illustration, partly as a block irnuit diagram, of a CT (computed tomography) apparatus wherein the inventive method for image reconstruction is employed.

The x-ray CT apparatus shown in FIG. 1 has a measuring unit composed of an x-ray source 1 that emits a fan-shaped x-ray beam 2 and a detector 3 that is composed of one or more lines of individual detectors, for example 512 individual detectors. The focus of the x-ray source I from which the x-ray beam 2 emanates is referenced 4. The examination subject 5, a human patient in the case of the exemplary embodiment, lies on a support table 6 that extends through the measuring opening 7 of a gantry 8.

The x-ray source 1 and the detector 3 are mounted to the gantry 8 opposite one another. The gantry 8 is seated rotatable around the z-axis of the CT apparatus, referenced z, that represents the system axis, and is rotated around the z-axis in the direction of the arrow a for scanning the examination subject 5 in the α-direction, namely by an angle $\alpha_g$ that amounts to at least 180° (Π) plus a fan angle $\beta_{fan}$(aperture angle of the fan-shaped x-ray beam 2). The x-ray beam 2 emanating from the x-ray source 1, operated with a voltage generator 9, covers a measuring field 10 having a circular cross-section. The focus 4 of the x-ray source 1 moves on a focus path 15 having the radius $R_F$ that is curved circularly around the rotational center lying on the z-axis.

Measured values are registered in the form of projections at specific angle positions of the measuring unit 1, 3, these angle positions being referred to as the projection angles. The corresponding measured values proceed from the detector 3 to an electronic calculating unit 11 that reconstructs the attenuation coefficients of the picture elements of a picture element matrix from sequences of measuring points corresponding to the projections, and graphically reproduces these on a viewing monitor 12 on which, thus, images of the transirradiated slices of the examination subject 5 appear.

Each projection S(β, α) is allocated to a specific angular position, a projection angle α, and covers a number of measuring points corresponding in number to the number of detector elements, i.e. the channel number, to which the corresponding measured value is respectively allocated. Each channel is defined by the appertaining fan angle β that indicates the detector elements from which the respective measured value originates.

When the detector 3 has multiple lines of detector elements, a number of slices of the examination subject 5 can be simultaneously registered as needed, with a number of projections corresponding in number to the number of active detector lines then being registered per projection angle.

The drive 13 allocated to the gantry 8 can be suitable not only for a sub-revolution or full revolution of the gantry 8, but also for continuously placing the gantry 8 into rotation. Another drive can be provided that enables a relative displacement between the support table 6 and thus the examination subject 5, and the gantry 8 with the measuring unit 1, 3, in the z-direction. Spiral scans thus can be implemented.

The CT apparatus according to FIG. 1 also has a known ECG apparatus 17 that can be connected to the examination subject 5 via electrodes—one thereof being shown in FIG. 1 and being referenced 18—, which serves for the acquisition of the ECG signal of the examination subject in parallel with the examination with the CT apparatus. Data corresponding to the ECG signal are supplied to the electronic calculating unit 11.

By contrast to a conventional CT apparatus wherein measured values from the range $\alpha_Q = \Pi + \beta_{fan}$, or $\alpha_Q = \Pi + \beta_{fan} + \alpha_{trans}$, are used in the image reconstruction for all channels, the electronic calculating unit 11 in the CT apparatus operates according to the inventive method for image reconstruction that is time-optimized and is described in greater detail below.

In a first operating mode described first, the CT apparatus operates in fan geometry; in a second operating mode described subsequently, it operates in parallel geometry.

Both operating modes are described for a detector line and can be analogously employed for multiple detector lines.

Instead of measured values from the range $\Pi + \beta_{fan}$ for all channels, only measured values from the channel-dependent, actually required region $$\alpha_g = \Pi - 2\beta \quad (5)$$

are used for the time-optimized inventive method in fan geometry. For time optimization, thus, the reconstructing data set is presented either by $$\hat{S}(\beta, \alpha) = \begin{cases} S(\beta, \alpha) & \alpha_0 \leq \alpha \leq \alpha_0 + \pi - 2\beta \\ & \text{for} \\ S(-\beta, \alpha + 2\beta - \pi) & \alpha_0 + \pi - 2\beta \leq \alpha \leq \alpha_0 + 2\pi; \end{cases} \quad \text{and} \quad (6)$$

as full data set, or by $$\overline{S}(\beta, \alpha) = \begin{cases} 2S(\beta, \alpha) & \alpha_0 \leq \alpha \leq \alpha_0 + \pi - 2\beta \\ & \text{for} \\ 0 & \alpha_0 + \pi - 2\beta \leq \alpha \leq \alpha_0 + 2\pi. \end{cases} \quad (7)$$

as an abbreviated data set (data set with fewer projections than necessary for a full revolution). In the above, $\alpha_0$ is the projection start angle in fan geometry, i.e. that projection angle at which the registration of projections begins given a sub-revolution, or the beginning angle with which measured values for image reconstruction are employed when values over a larger projection angle range are acquired than are necessary solely for producing an image measured. In total, measured values from the measuring time interval $$t_{Q,opt} = \frac{\pi - 2\beta}{2\pi} t_{rot}$$

are employed for each detector channel identified by β. For subjects in the proximity of the rotational center, only detector elements having β≈0 contribute to the image. The time resolution in the rotational center therefore amounts to $t_{Q,opt} \approx 0.5\ t_{rot}$. The time resolution $t_{Q,opt}$ can be greater or smaller then half the revolution time outside the rotational center. This can be seen in the sinugram according to FIG. 2, wherein the fan angle β is entered with respect to the projection angle α, wherein the minimally required projection angle range for a channel β>0 (upper dot-dashed line) is reached sooner than for a channel β<0 (lower dot-dashed line). Reaching the minimally required projection angle range can be recognized by the interaction of the dot-dashed lines with the solid straight line A-B.

The size of the measuring time interval that contributes to a specific picture element is shall be described in greater detail below.

For reducing artifacts due to movements or axial inhomogeneities, transition regions having the width $\alpha_{trans}$ are inserted. A smooth transition function g(α) that varies from 0 to 1 between 0 and $\alpha_{trans}$ is introduced into these transition regions. A suitable function g(α) in the case of the present exemplary embodiment is $$g(\alpha) = \sin^2 \frac{\pi(\alpha - \alpha_0)}{2\alpha_{trans}}, \quad (8)$$

Other transition functions are not precluded. One thus ultimately obtains $$\hat{S}(\beta, \alpha) = \begin{cases} g(\alpha)S(\beta, \alpha) + (1 - g(\alpha))S(-\beta, \alpha + 2\beta - \pi) & \alpha_0 \leq \alpha \leq \alpha_0 + \alpha_{trans} \\ S(\beta, \alpha) & \alpha_0 + \alpha_{trans} \leq \alpha \leq \alpha_0 + \pi - 2\beta \\ (1 - g(\alpha - \pi + 2\beta))S(\beta, \alpha) & \text{for} \\ +g(\alpha - \pi + 2\beta)S-(-\beta, \alpha + 2\beta - \pi) & \alpha_0 + \pi - 2\beta \leq \alpha \leq \alpha_0 + \pi - 2\beta + \alpha_{trans} \\ S(-\beta, \alpha + 2\beta - \pi) & \alpha_0 + \pi - 2\beta + \alpha_{trans} \leq \alpha \leq \alpha_0 + 2\pi; \text{ and} \end{cases} \quad (9)$$

for the presentation of a full data set. If, following the discretization of this equation to a measured value at the location $\beta_k$, no measured value is present at the location $-\beta_k$, this can be acquired, for example, by interpolation. However, one can again switch to the abbreviated data set, $$\ddot{S}(\beta, \alpha) = \begin{cases} 2g(\alpha)S(\beta, \alpha) & \alpha_0 \leq \alpha \leq \alpha_0 + \alpha_{trans} \\ 2S(\beta, \alpha) & \alpha_0 + \alpha_{trans} \leq \alpha \leq \alpha_0 + \pi - 2\beta \\ & \text{for} \\ 2(1 - g(\alpha - \pi + 2\beta))S(\beta, \alpha) & \alpha_0 + \pi - 2\beta \leq \alpha \leq \alpha_0 + \pi - 2\beta + \alpha_{trans} \\ 0 & \alpha_0 + \pi - 2\beta + \alpha_{trans} \leq \alpha \leq \alpha_0 + 2\pi. \end{cases} \quad (10)$$

The data sets $\hat{S}(\beta, \alpha)$ or $\bar{S}(\beta,\alpha)$ according to Equation 9 or 10 are then processed by the calculating unit 11 with a fan image reconstruction of a known type, for example, a convolution back-projection reconstruction.

The measured values $S(\beta, \alpha)$ can be sub-revolution data with a revolution angle of adequate size or single or multiple revolution data. By contrast to the image calculation from sequential sub-revolution exposures, the problem of dose utilization is reduced in importance because an adequate number of images can be calculated at different points in time.

When the CT apparatus operates in the second operating mode, i.e. according to parallel geometry, parallel data $S(p,\Theta)$ are generated from the measured values $S(\beta, \alpha)$ acquired in fan geometry by a standard re-binning of a known type. Azimuthal and radial interpolation (re-binning) is thereby also based on the following relationship $$\Theta = \alpha + \beta - \Pi/2, \quad p = R_F \sin \beta \quad (11)$$

wherein $R_F$ is the distance of the focus 4 from the rotational center. The equality $$\alpha(t) = \alpha_0 + \frac{2\pi}{t_{rot}} t. \quad (12)$$

continues to apply. Even when the fan projection angle $\alpha$ of the input data covers the regular sub-revolution interval $\alpha_Q \Pi + \beta_{fan} + \alpha_{trans}$, parallel data are calculated only for the parallel projection interval $$\Theta_{Q,opt} = \alpha_{trans} + \Pi \quad (13)$$

The equality $\Theta_0 \leq \Theta \leq \Theta_0 + \alpha_{trans} + \Pi$ is thus valid for the parallel projection angle ($\Theta_0$ is the start angle of the reconstruction in parallel geometry that derives from $\alpha_0$). The remainder of the parallel data is not used. The azimuthal interpolation from $\alpha$ to $\Theta$ is schematically shown in FIG. 3.

Figure 3:
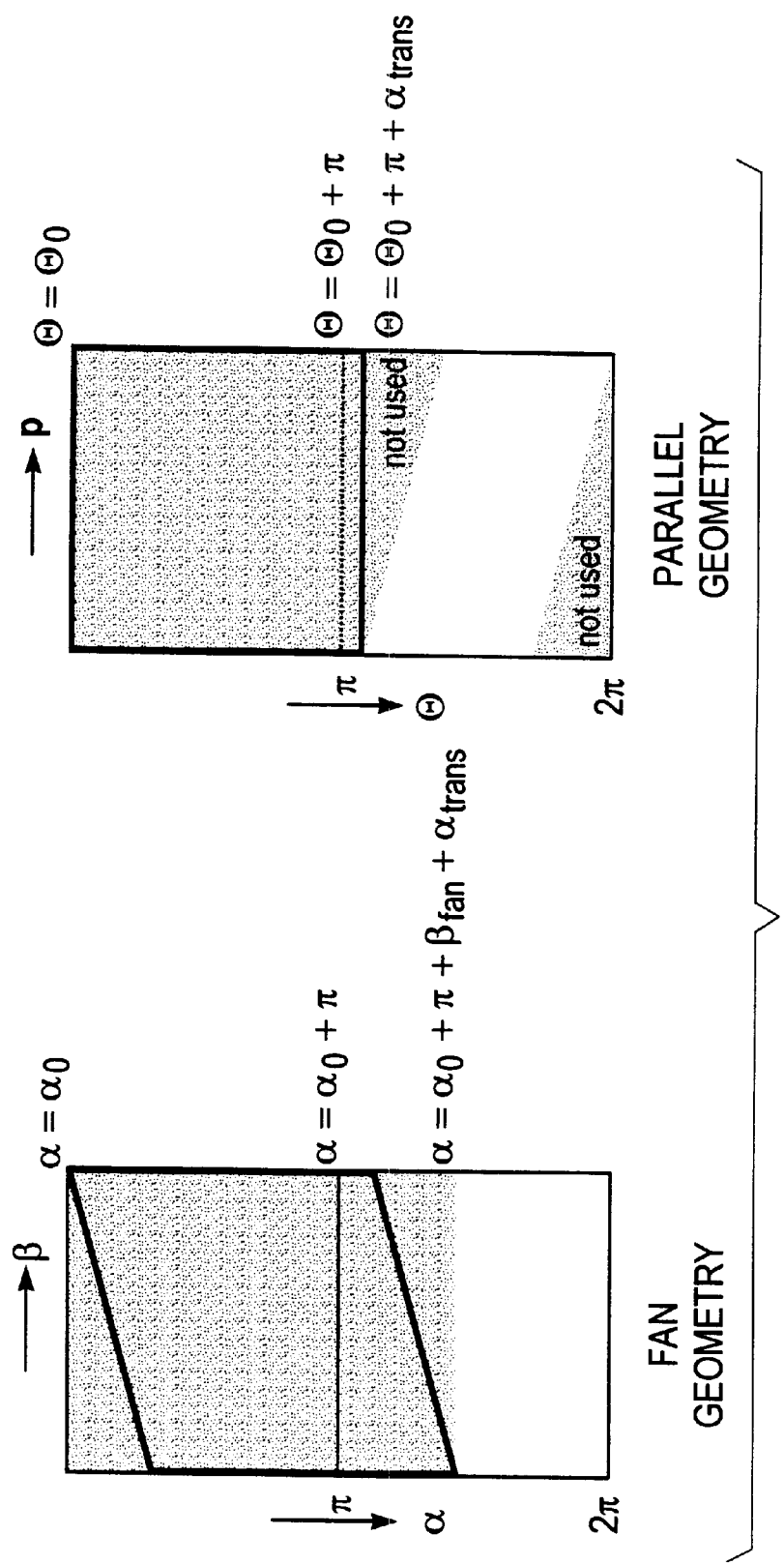
FIG. 3 shows the dependency of the time-sensitivity profile on the relationship between picture element and reconstruction start angle given fan reconstruction.

At the left, FIG. 3 shows a sinugram in fan geometry. In this, the fan angle $\beta$ of the measured values is entered toward the right and the fan projection angle $\alpha$ is entered toward the bottom. The projection angle $\alpha$ covers the regular sub-revolution interval $\alpha_Q$. Parallel data for a constant $\Theta$ lie on slanting lines in this sinugram. The corresponding sinugram in parallel geometry is shown at the right in FIG. 3. Here, the coordinate p is entered toward the right and the parallel projection angle $\Theta$ is entered toward the bottom. The projection angle range $\Theta^{Q,opt}$ employed is shown bounded in bold face.

The measured values employed are thus limited to the measuring time interval $$t_{Q,opt} = \frac{\theta_{Q,opt}}{2\pi} t_{rot} \quad (14)$$

for each detector channel identified by a specific p. The time intervals for different p are shifted relative to one another on an absolute time axis. For objects in the proximity of the rotational center, only detector elements having $p \approx 0$ contribute to the image. The time resolution in the rotational center therefore amounts to $t_{Q,opt} \approx 0.5\, t_{rot}$. Detector elements having various values of p contribute to the image for objects lying outside the rotational center; the time resolution that is then achieved shall be explained in greater detail below.

In order to avoid line artifacts due to moving subjects and similar data inconsistencies, the parallel projections in the angular range $\Theta_0 \leq \Theta \leq +\alpha_{trans} + \Pi$ are again subjected to a weighting and are combined onto the angular range $\Theta_0 \leq \Theta \leq \Theta_0 + \Pi$, with $$g(\Theta) = \sin^2\left(\pi\Theta - \frac{\Theta_0}{2\alpha_{trans}}\right). \quad (15)$$

used as a weighting function in the described exemplary embodiment, but other weighting functions are possible. Parallel data $S_\Pi(p, \Theta)$ in the projection angle interval $\Theta_0 \leq \Theta \leq \Theta_0 + \Pi$ are calculated with this weighting function $g(\Theta)$:

$$S_\pi(p, \Theta) = \begin{cases} g(\Theta)S(p, \Theta) + (1 - g(\Theta))S(-p, \Theta + \pi) & \Theta_0 \le \Theta \le \Theta_0 + \alpha_{trans} \\ \text{for} & \\ S(p, \Theta) & \Theta_0 + \alpha_{trans} \le \Theta \le \Theta_0 + \pi \end{cases} \quad (16)$$

If, following the discretization of this equation, no measured value is present at the location $-p_k$ for a measured value at the location $p_k$, this can be approximated, for example, by interpolation. The data $S_\Pi(p, \Theta)$ are processed by the calculating unit 11 using a known parallel image reconstruction, for example, according to a convolution back-projection reconstruction.

With the inventive method, the time resolution becomes dependent on the point observed in the image plane and on the projection start angle of the reconstruction. This is explained separately below for fan and parallel geometry.

In order to describe the time behavior, the concept of the time sensitivity profile $P(t, \underline{r})$ is used. This profile is the reaction of the system to a temporally δ-like event (dirac function) at the location r in the measuring field. The profile is derived from the normalized, weighted superimposition of the time structure of the individual measured values h(t), taking the filtered curve of the data acquisition system into consideration (detector and following electronics=DAS). The weightings $H(\alpha(t), \underline{r})$ are derived from the respective reconstruction rule. In general, one obtains $$P(t, r) = \frac{\int H(\alpha(t'), \underline{r}) h(t - t') \left| \frac{d\alpha}{dt}(t') \right| dt'}{\int H(\alpha(t'), \underline{r}) \left| \frac{d\alpha}{dt}(t') \right| dt'} \quad (17)$$

Given an image reconstruction in fan geometry, the cos weighting, the $1/R^2$ and the weightings $g(\alpha)$ enter into the determination of the time sensitivity profile. When a picture element having the polar coordinates $\underline{r}=(r, \phi)$ is observed, then the following is valid:

$$P(\underline{r}, t) = \frac{\int \frac{1}{R^2(\alpha(t'), \underline{r})} \cos\Phi(\alpha(t'), \underline{r}) g(\alpha(t'), \Phi(\alpha(t'), \underline{r})) h(t - t') \left| \frac{d\alpha}{dt} \right| dt'}{\int \frac{1}{R^2(\alpha(t'), \underline{r})} \cos\Phi(\alpha(t'), \underline{r}) g(\alpha(t'), \Phi(\alpha(t'), \underline{r})) \left| \frac{d\alpha}{dt} \right| dt'} \quad (18)$$

Thereby, $$R^2(\alpha, \underline{r}) = R_F^2 + r^2 - 2rR_F \cos(\alpha - \phi) \quad (19)$$

is the square of the focus-to-picture element spacing and $\phi(\alpha, \underline{r})$ is the fan angle of the picture element, $$\phi(\alpha, \underline{r}) = \arcsin\left(\frac{r'}{R(\alpha, \underline{r})} \sin(\alpha - \phi)\right) \quad (20)$$

As a result of Equation (12), the derivative of α with respect to time t is a constant, $d\alpha/dt = 2\Pi/t_{rot}$. This constant drops out of equation (18) due to abbreviation.

Figure 2:
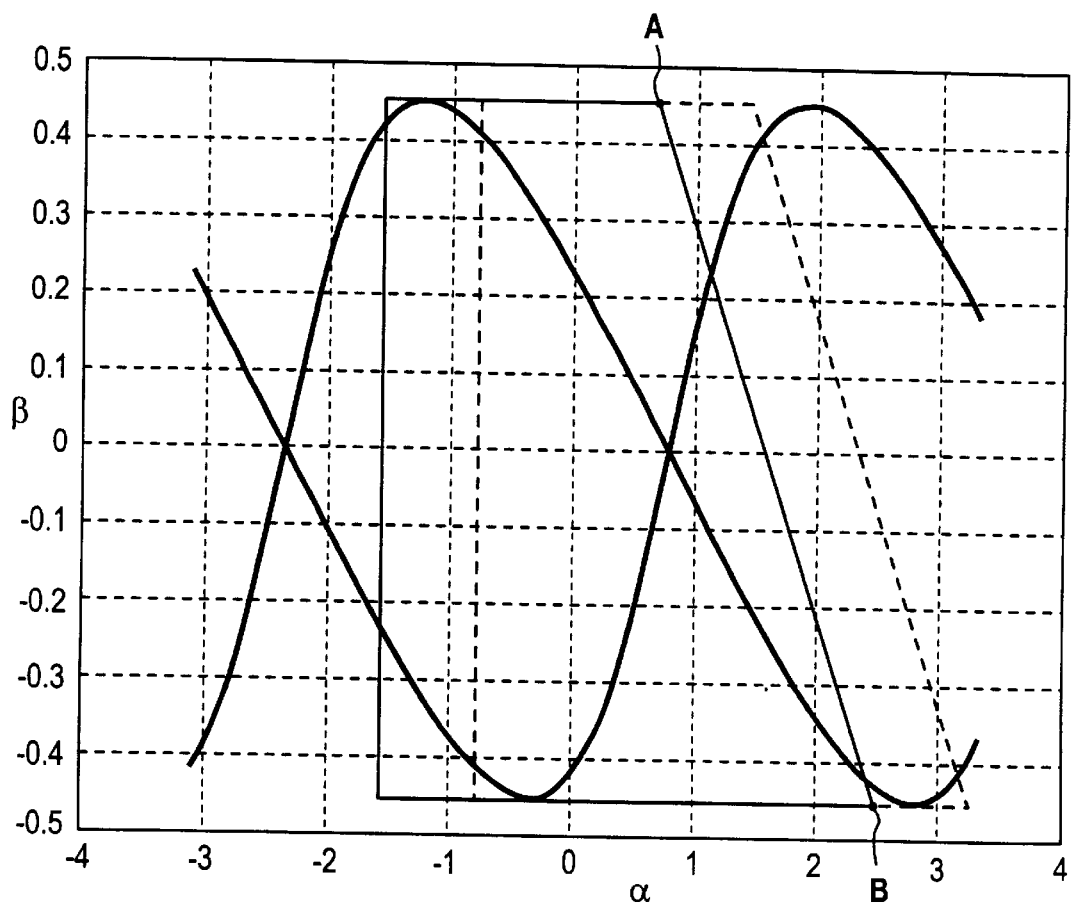
FIG. 2 shows sinugrams for two different points in the image field for illustrating the location-dependent time resolution in the inventive method in the case of image reconstruction in fan geometry.
Figure 4:
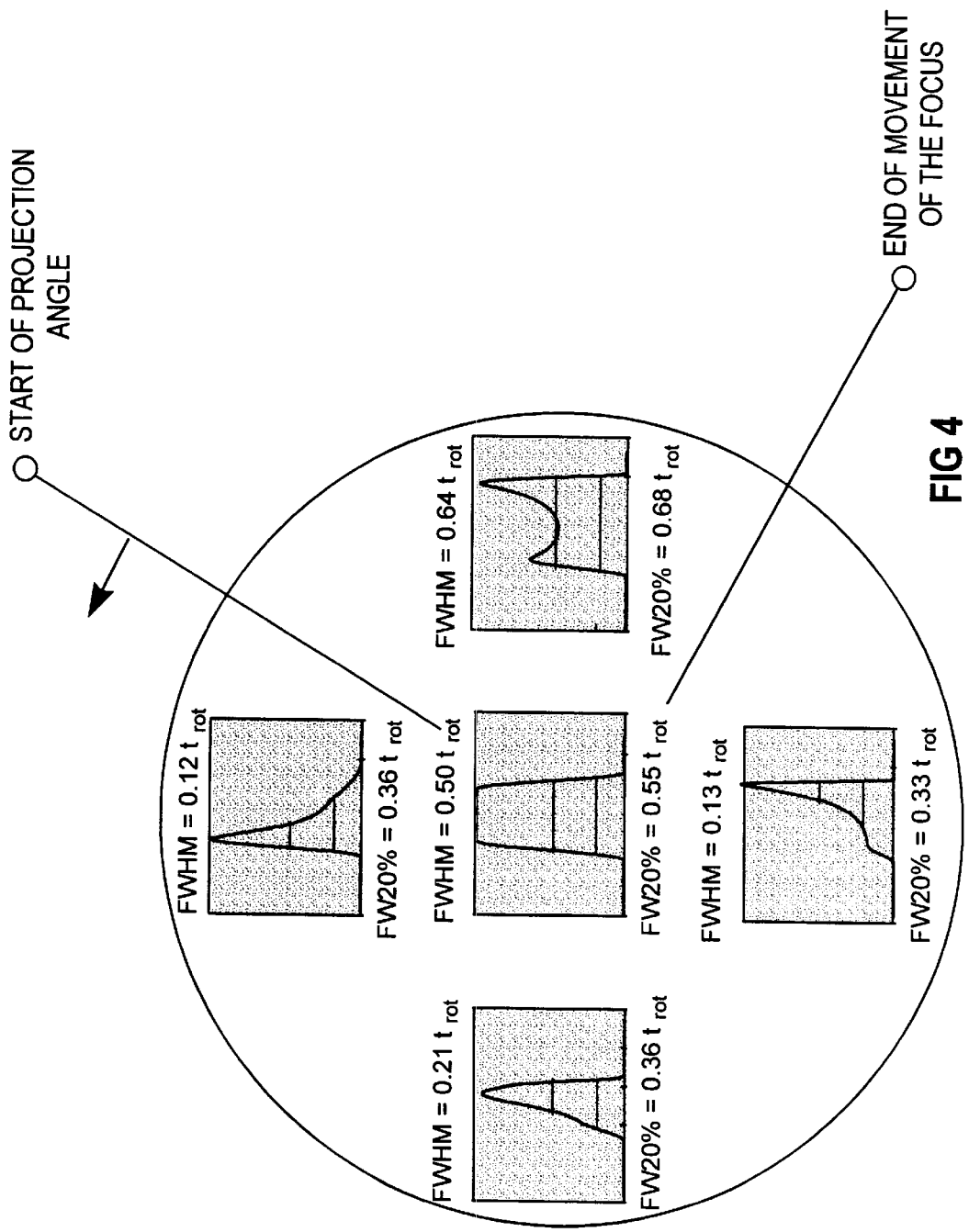
FIG. 4 is a comparison of the sinugrams for fan and parallel geometry given sub-revolution reconstruction on the basis of the inventive method.

The curve of $\phi(\alpha, \underline{r})$ for two specific picture elements can be seen in FIG. 2 as respective solid sine-like lines. Results of corresponding observations for various picture elements are shown in FIG. 4. Various time-sensitivity profiles are shown, as a function of the position of the appertaining picture element in the measuring field, wherein the measured value caused in a time sensitivity profile by a temporally δ-like event is entered as a dimensional quantity over the time, and wherein the middle of the time axis corresponds to the occurrence of the event. The value $\alpha_0 = \Pi/2 - \beta_{fan}/2$ was selected as the start angle, as well as $\alpha_{trans} = \Pi/4$. The vidth of the time sensitivity profile given one-fifth of the maximum amplitude (FW 20%) varies over the measuring field from 0.36 $t_{rot}$ through 0.71 $t_{rot}$. In particular, a better time resolution than half the revolution time can be achieved in parts of the measuring field with the inventive method. The spatial distribution of the time resolution is coupled to the start angle, i.e. an especially good time resolution can be set in specific regions of the measuring field by intentional selection of the start angle. Moreover, the full width at half maximum FWHM of the time sensitivity profile is also entered in FIG. 3.

Given fan reconstruction, the time resolution In the image center thus can be reduced to approximately half the revolution time with the inventive method. The time resolution can be shorter or longer at other locations in the image.

Given the image reconstruction of fan data in parallel geometry, only the weightings $g(\Theta)$ enter into the determination of the time sensitivity profile. When a picture element having the polar coordinates $\underline{r}=(r, \phi)$ is again considered, then the following applies:

$$P(\underline{r}, t) = \frac{\int g(\Theta(t'), \Phi(\Theta(t'), \underline{r})) h(t - t') \left| \frac{d\Theta}{dt} \right| dt'}{\int g(\Theta(t'), \Phi(\Theta(t'), \underline{r})) \left| \frac{d\Theta}{dt} \right| dt'} \quad (21)$$

Due to $\Theta = \alpha + \beta - \Pi/2$, one obtains $$\Theta(t) = \alpha_0 + \frac{2\pi}{t_{rot}} t + \arcsin\left(\frac{r}{R\left(\alpha_0 + \frac{2p}{t_{rot}} t, \underline{r}\right)} \sin\left(\alpha_0 + \frac{2p}{t_{rot}} t - j\right)\right) - \pi/2. \quad (22)$$

with equations (12) and (20). The derivative $d\Theta/dt$ can be calculated therefrom, which now is no longer being a time constant due to the conversion of fan to parallel geometry. It must be taken into consideration in the integrations in Equation (21), and is responsible for the picture element dependency of the time sensitivity profile in the parallel reconstruction.

At the left, FIG. 3 shows a sinugram for fan geometry and, at the right, shows a sinugram for parallel geometry with the data regions employed for the reconstruction. A sinugram for fan geometry for two picture elements is entered in FIG. 5, namely for r=25 cm, $\phi=\Pi$ (left) and for r=25 cm, $\phi=\Pi/2$ (right). In both instances, the reconstruction start angle is $\alpha_0 = \Pi/2$. Moreover, $R_F = 57$ cm applies. The data region employed for the inventive parallel reconstruction is marked by hatching (also see FIG. 3). The fan projection angle $\alpha$ determines the point in time at which a measured value was registered, since Equation (12) applies. The time axis thus proceeds parallel to the $\alpha$-axis.

Figure 5:
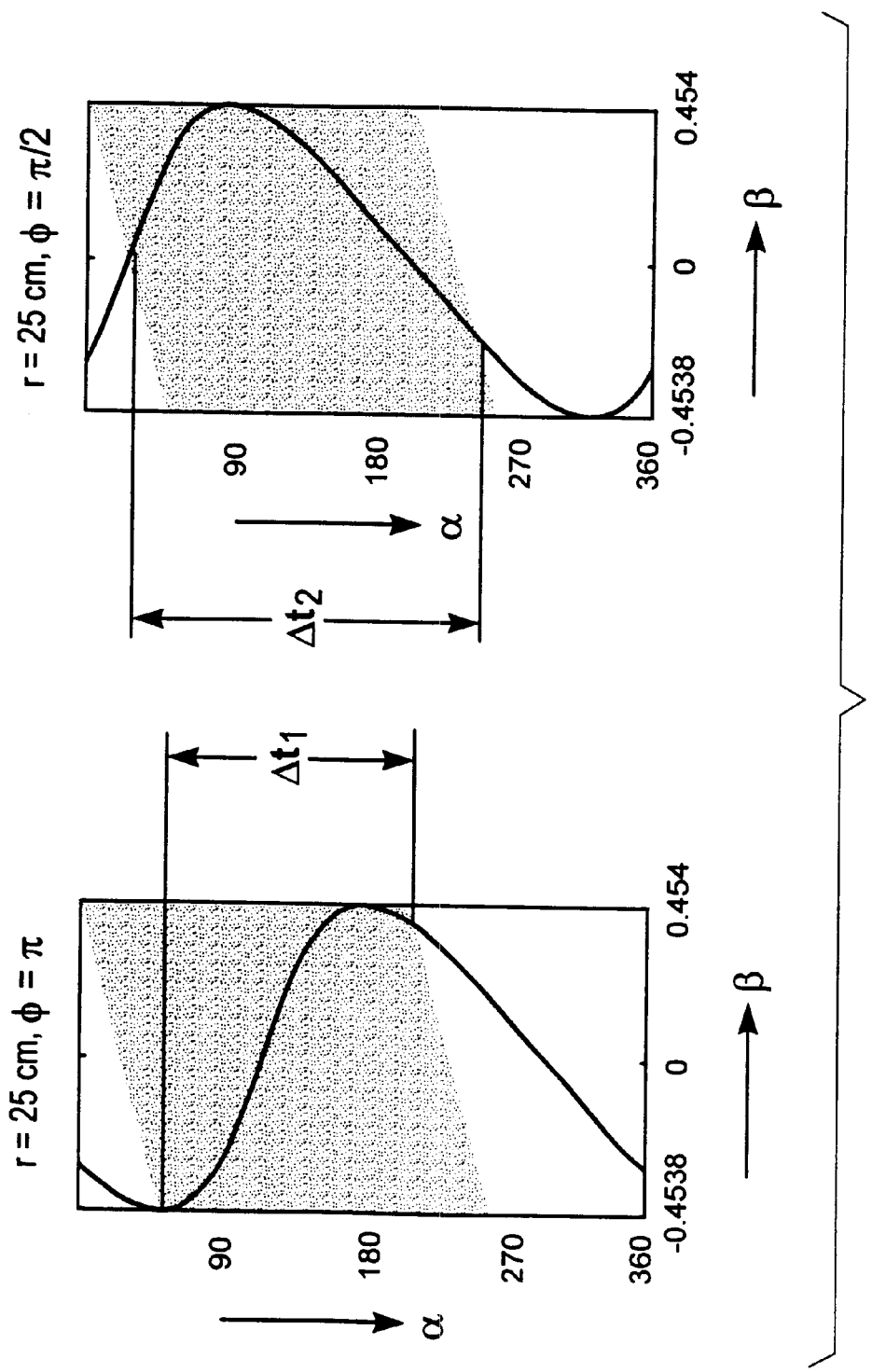
FIG. 5 shows sinugrams for two different points in the image field for illustrating the location-dependent time resolution given the inventive method in the case of image reconstruction in parallel geometry.

It can be seen from FIG. 5 that a shorter time window contributes to the reconstruction of the picture element r=25 cm, $\phi = \Pi$ than to the reconstruction of the picture elements r=25 cm, $\phi = \Pi/2$, since $\Delta t_1 < \Delta t_2$ applies. Accordingly, time sensitivity profiles that are dependent on the relationship between picture element and the start position of the focus of the x-ray source also arise in the parallel reconstruction of fan data, as shown in FIG. 6. Various time sensitivity profiles are shown as function of the position of the appertaining picture element in the measuring field. The value $\alpha_0 = \Pi/2 - \beta_{fan}/2$ was again selected as start angle, as was $\alpha_{trans} = \Pi/3$. The width of the time sensitivity profile given one-fifth of the maximum amplitude varies over the measuring field from 0.375 $t_{rot}$ through 0.675 $t_{rot}$. Again, a better time resolution than half the revolution time can be achieved in parts of the measuring field with the inventive method.

Thus the time resolution in the image center can be reduced to approximately half the revolution time with the inventive method for parallel reconstruction.

As a result of the acquisition of the ECG signal of the examination subject 5, it is possible in a corresponding operating mode of the CT apparatus according to FIG. 1 to select the reconstruction start and angle, taking the QRS complex of the ECG signal into consideration so that the measured values utilized for the reconstruction of an image of the heart or of heart-proximate body regions of the examination subject are registered during the desired phase of the heart cycle, preferably during a resting phase. A number of images thus can be reconstructed for selected time emphases on the basis of the ECG from measured values acquired with a single or multiple revolution.

When only a sub-revolution occurs for the examination, there is also the possibility in another operating mode of the CT apparatus according to FIG. 1 to trigger the beginning of the sub-revolution with the ECG signal, namely such that the measured values of the sub-revolution are acquired during a desired phase of the heart cycle of the subject.

Moreover, the CT apparatus according to FIG. 1 can be operated in an operating mode so that more measured values are acquired than are required solely for reconstruction of an image (overscan data set), and an image is then reconstructed from these measured values by suitable selection of the reconstruction start angle. This image exhibits a desired time resolution for a specific picture element or a specific diagnostically relevant region that is referenced ROI in FIG. 1, and preferably exhibits the maximally possible time resolution for this picture element or region. There is thereby also the possibility of reconstructing a number of images for different time emphases from measured values acquired in a single or multiple revolution.

The inventive method was explained above with reference to the example of a computed tomography apparatus of the third generation, however, it can also be employed to operate computed tomography systems of the fourth generation.

The inventive method can be employed not only in the medical field, as in the case of the exemplary embodiment. Applications in the non-medical area are also within the scope of the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for image reconstruction in a computed tomography system, comprising the steps of:
   obtaining measured values $S(\beta, \alpha)$ in fan geometry by rotating a focus of a radiation source around a system axis and around a measuring field accepting an examination subject, said measured values being individually characterized by a projection angle $\alpha$ and a fan angle $\beta$, and employing only a minimally possible projection angle range $\alpha_g(\beta)$ for a respective fan angle $\beta$ for all measured values $S(\beta,\alpha)$ of that respective fan angle $\beta$, said minimally possible projection angle range $\alpha_g(\beta)$ being $\alpha_g(\beta) = \Pi - 2\Omega\beta$; and
   reconstructing an image having a time resolution from said measured values, and selecting said time resolution by at least one of:
   positioning the examination subject in the measuring field before obtaining said measured values so that a diagnostically relevant region of the examination subject lies in a region of the measuring field wherein a desired time resolution that deviates from other regions of the measuring field, is present,
   obtaining said measured values for projection angles so that a desired time resolution that deviates from other regions of the measuring field exists in that region of the measuring field wherein a diagnostically relevant region of the examination subject is located, and
   obtaining more measured values than are required solely for image reconstruction of a diagnostically relevant region of the examination subject, and conducting the image reconstruction using measured values selected so that a desired time resolution, that deviates from other regions of the measuring field, exists in that region of the measuring field wherein the diagnostically relevant region is located.

2. A method according to claim 1, wherein a higher time resolution exists in the region of the measuring field having said desired time revolution deviating from other regions of the measuring field.

3. A method according to claim 1 comprising, for reducing motion or spiral artifacts, using measured values from a freely selectable transition region having a width $\alpha_{trans}$ for reconstructing said image in addition to the minimally possible projection angle range $\alpha_g(\beta)$.

4. A method according to claim 1 comprising obtaining the measured values $S(\beta, \alpha)$ during a sub-revolution of the focus of the radiation source.

5. A method according to claim 4, comprising obtaining the measured values while displacing the radiation source and the examination subject relative to one another in the direction of the system axis.

6. A method according to claim 1 comprising obtaining the measured values $S(\beta, \alpha)$ during a single revolution of the focus of the radiation source.

7. A method according to claim 6, comprising obtaining the measured values while displacing the radiation source and the examination subject relative to one another in the direction of the system axis.

8. A method according to claim 1, comprising obtaining the measured values $S(\beta, \alpha)$ during multiple revolutions of the focus of the radiation source.

9. A method according to claim 8, comprising obtaining the measured values while displacing the radiation source and the examination subject relative to one another in the direction of the system axis.

10. A method according to claim 1 comprising reconstructing said image in fan geometry.

11. A method for according to claim 1 comprising reconstructing said image in parallel geometry using re-binning of said measured values.

12. A method according to claim 1 comprising reconstructing a plurality of images with time spacings from one another suitable for cinematic presentation.

13. A method according to claim 1 comprising reconstructing said image using measured values acquired during a measuring time interval, obtaining an ECG signal, containing a QRS complex, of the examination subject, while obtaining the measured values, and determining and adjusting a time position of said measuring time interval dependent on the QRS complex of the ECG signal.

14. A method for image reconstruction according to claim 1 comprising reconstructing said image using measured values acquired during a measuring time interval, obtaining an ECG signal of the examination subject while obtaining the measured values, and triggering a beginning of the measuring time interval by the ECG signal.

* * * * *